US000001892H

United States Statutory Invention Registration [19]

[11] Reg. Number: H1,892

Klein et al. [45] Published: Oct. 3, 2000

[54] HIGH VOLUME NUTRIENT BASED YEAST TWO-HYBRID ASSAY FOR THE IDENTIFICATION OF SPECIFIC PROTEIN:PROTEIN INTERACTING INHIBITORS

[75] Inventors: Ronald D. Klein, Schoolcraft; Jerry M. Buysse, Portage, both of Mich.

[73] Assignee: Pharmacia and Upjohn Company, Kalamazoo, Mich.

[21] Appl. No.: 08/684,612

[22] Filed: Jul. 19, 1996

Related U.S. Application Data

[60] Provisional application No. 60/006,475, Nov. 13, 1995, and provisional application No. 60/001,585, Jul. 27, 1995.

[51] Int. Cl.[7] ..... C12P 21/06

[52] U.S. Cl. ..... 435/69.1

[58] Field of Search ..... 435/6, 29, 30, 435/69.1

[56] References Cited

U.S. PATENT DOCUMENTS

| | | | |
|---|---|---|---|
| 4,833,080 | 5/1989 | Brent | 435/172.3 |
| 5,079,143 | 1/1992 | Klein | 435/29 |
| 5,283,173 | 2/1994 | Fields | 435/6 |
| 5,468,614 | 11/1995 | Fields et al. | 435/6 |
| 5,525,490 | 6/1996 | Erickson et al. | 435/29 |
| 5,539,085 | 7/1996 | Bischoff et al. | 530/350 |
| 5,610,015 | 3/1997 | Wickens et al. | 435/6 |

OTHER PUBLICATIONS

Mendelsohn et al. 1994, vol. 5, No. 5, pp. 482–486, Oct. 1994.
Sikorski et al. 1991. Methods of Enzymology, vol. 194, pp. 302–318, 1991.
Fields, S., et al., 1994, Trends in Genetics, vol. 10, No. 8, pp. 286–292, Aug. 1994.
Chien, C.–T., *Proc. Natl. Acad. Sci. , USA*, 88:9578–82 (1991).
Allen, G. C., Jr., *J. Biol. Chem.*, 266:22096–22101 (1991).
Arai, K.I., *J. Biol. Chem.*, 256:5281–5286 (1981).
Bartel, P. L., In: Cellular Interactions and Development: A Practical Approach, pp. 153–179 (1993a).
Bartel, P., *BioTechniques*, 14:920–924 (1993b).
Brent, R., *Cell*, 43:729–736 (1985).
Coghlan, V.M., et al., *Science*, 267:108–111 (1995).
Durfee, T. K., et al., *Genes and Dev.*, 7:555–569.
Elledge, S. J., et al., *Proc. Natl. Acad. Sci. USA*, 88:1731–1735 (1991).
Feilotter, H. E., et al., *Nucleic Acids Res.*, 22:1502–1503 (1994).
Fields, S., et al., *Trends in Genetics*, 10:286–292 (1994).
Fields, S., et al., *Nature*, 340:245–246 (1989).
Finely, R. L., et al., *Proc. Natl. Acad. Sci. USA*, 91:12980–12984 (1994).
Golemis, E. A., et al., *Molec. Cell. Biol.*, 12;3006–3014 (1992).
Hiasa, H., et al., *J. Biol. Chem.* 267:11379–11385 (1992).
Harper, J. W., et al., *Cell*, 75:805–816 (1993).
Helps, N. R., et al., *FEBS Lett.*, 340:93–98 (1994).
Hill, C. W., et al., *Proc. Natl. Acad. Sci. USA*, 78:7069–7072 (1982).
Hoeffler, J.P., et al., *J. Cell. Biochem.*, Suppl. 18D, 190 (1994).
Johnson, M., et al., *Molec. Cell. Biol.*, 4, pp. 1440–1448 (1984).
Kalpana, G.V., et al., *Science*, 266, pp. 2002–2006 (1994).
Keegan, L., et al., *Science*, 231, pp. 699–704 (1986).
Klein, R. D. et al., *Curr. Genet.*13, pp. 29–35 (1989a).
Klein, R. D. et al., *Curr. Genet.*, 16, pp. 145–152 (1989b).
Klopotowski, T. et al., *Arch. Biochem. Biophys.*, 112, pp. 562–566 (1965).
LeDouarin, B. et al., *Nucleic Acids Res.*, 23, 5, pp. 876–878 (1995).
Li, B. et al., *FASEB J.*, 7, pp. 957–963 (1993).
Lorch, Y. et al., *J. Mol. Biol.*, 186, pp. 821–824 (1984).
Luban, J. et al., *Cell*, 73, pp. 1067–1078 (1993).
Ma, J. et al., *Cell*, 48, pp. 847–853 (1987).
Marszalek, J. et al., *J. Biol. Chem.*, 269, pp. 4883–4890 (1994).
Morin, P. J. et al., *Nucleic Acids Res.*, 21, pp. 2157–2163 (1993).
Paetkau, D. W. et al., *Genes and Dev.*, 8, pp. 2035–2045 (1994).
Sato, T. et al., *Proc. Natl. Acad. Sci. USA.,* 91, pp. 9238–9242 (1994).
Spaargaren, M. et al., *Proc. Natl. Acad. Sci. USA.,* 91, 12609–12613 (1994).
Stukenberg, P. T. et al, *Cell*, 78, pp. 877–887 (1994).
Tougu, K. et al., *J. Biol. Chem.*, 269, pp. 4675–4682 (1994).
Vojtek, A. B. et al., *Cell*, 74, pp. 205–214 (1993).
Wickner, S. et al., *Proc. Natl. Acad. Sci. USA*, 72, pp. 921–925 (1975).
Yang, M. et al., *Nuc. Acids Res.*, 23, 7, pp. 1152–1156 (1995).
Ye, Z. S. et al., *Proc. Natl. Acad. Sci. USA*, 91, pp. 12629–12633 (1994).
Yeung, K. C. et al., *Genes and Dev.*, 8, pp. 2097–2109 (1994).
Zang, X–F. et al., *Nature*, 364, pp. 308–313 (1993).

*Primary Examiner*—Charles T. Jordan
*Assistant Examiner*—Meena Chelliah
*Attorney, Agent, or Firm*—Thomas A. Wootton

[57] ABSTRACT

This invention describes how to make and use several effective high volume screens for the discovery of inhibitors of specific protein:protein interactions, using aspects of the yeast two-hybrid system.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HIGH VOLUME NUTRIENT BASED YEAST TWO-HYBRID ASSAY FOR THE IDENTIFICATION OF SPECIFIC PROTEIN:PROTEIN INTERACTING INHIBITORS

CROSS-REFERENCE TO RELATED APPLICATIONS

This application claims the benefit of U.S. provisional application Ser. Nos. 60/006,475 filed Nov. 13, 1995 and 60/001,585 filed July 27, 1995.

FIELD OF THE INVENTION

This invention relates to the fields of the yeast two-hybrid system, and nutrient based screens and assays to detect inhibitors of protein:protein interactions such as: bacterial metabolic systems that rely on specific protein interactions for normal function and metabolic systems found in bacterial DNA replication. The system is expected to work as well with other protein complexes.

INFORMATION DISCLOSURE

U.S. Pat. No. 5,283,173, issued Feb. 1, 1994, inventor, Stanley Fields, "System to Detect Protein-Protein Interactions."

U.S. Pat. No. 5,079,143, issued Jan. 7, 1992, inventor, Ronald D. Klein, "Method of Identifying Compounds Useful as Antiparasitic Drugs."

U.S. Pat. No. 4,833,080, issued May 23, 1989, inventor, Roger Brent and Mark S. Ptashne, "Regulation of Eucaryotic Gene Expression."

Chien C. T., Bartel P. L. Sternglanz R., and S. Fields (1991) The two-hybrid system: a method to identify and clone gene for troeins that interact with a protein of interest. *Proc. Natl. Acad. Sci. U.S.A.* 21: 9578–82

Allen, G. C., Jr. and A. Kornberg (1991) Fine balance in the regulation of DnaB helicase by DnaC protein in replication in *Escherichia coli. J. Biol. Chem.* 266:22096–22101.

Arai, K. I., R. McMacken, S. I. Yasuda and A. Kornberg (1981) Purification and properties of *Escherichia coli* protein: a prepriming protein in phage ϕX174 DNA replication. *J. Biol. Chem.* 256:5281–5286.

Ausubel, F. M., R. Brent, R. E. Kingston, D. D. Moore, J. G. Seidman, J. A. Smith and K. Struhl (1994) Current Protocols in Molecular Biology. John Wiley and Sons, New York, N.Y.

Bartel, P. L., C-T. Chien, R. Sternglanz and S. Fields (1993a) Using the two-hybrid system to detect protein-protein interactions. In: Cellular Interactions and Development: A Practical Approach, ed. D. A. Hartley, Oxford University Press, Oxford. pp. 153–179.

Bartel, P., C-T. Chien, R. Sternglantz and S. Fields (1993b) Elimination of false positives that arise in using the two-hybrid system. *BioTechniques* 14:920–924.

Brent, R. and M. Patashne (1985) A eucaryotic transcriptional activator bearing the DNA specificity of a procaryotic repressor. *Cell* 43:729–736.

Chien, C-T., P. L. Bartel, R. Sternglanz and S. Fields (1991) The two-hybrid system: A method to identify and clone genes for proteins that interact with a protein of interest. *Proc. Natl. Acad. Sci. USA* 88:9578–9582.

Coghlan, V. M., B. A. Perrino, M. Howard, L. K. Langeberg, J. B. Hicks, W. M. Gallatin and J. D. Scott (1995) Association of protein kinase A and protein phosphatase 2B with a common anchoring protein. Science 267:108–111.

Durfee, T., K. Becherer, P-L. Chen, S-H. Yeh, Y. Yang, A. E. Kilburn, W-H. Lee and S. J. Elledge (1993) The retinoblastoma protein associates with the protein phosphatase type 1 catalytic subunit. *Genes and Dev.* 7:555–569.

Elledge, S. J., J. T. Mulligan, S. W. Ramer, M. Spottswood and R. W. Davis (1991) λYES: A multifunctional cDNA expression vector for the isolation of genes by complementation of yeast and *Escherichia coli* mutations. *Proc. Natl. Acad. Sci. USA* 88: 1731–1735.

Feilotter, H. E., G. J. Hannon, C. J. Ruddell and D. Beach (1994) Construction of an improved host strain for two hybrid screening. *Nucleic Acids Res.* 22:1502–1503.

Fields, S. and R. Sternglanz (1994) The Two Hybrid system: an assay for protein-protein interactions. Trends *in Genetics* 10:286–292.

Fields, S. and O. Song (1989) A novel genetic system to detect protein-protein interactions. *Nature* 340:245–246.

Finley, R. L. and R. Brent (1994) Interaction mating reveals binary and ternary connections between Drosophila cell cycle regulators. *Proc. Natl. Acad. Sci. USA* 91:12980–12984.

Golemis, E. A. and R. Brent (1992) Fused protein domains inhibit DNA binding by Lex A. *Molec. Cell. Biol.* 12:3006–3014.

Hiasa, H. and K. J. Marians (1992) Differential inhibition of the DNA translocation and DNA unwinding activities of DNA helicases by the *Escherichia coli* Tus protein. *J. Biol. Chem.* 267:11379–11385.

Harper, J. W., G. R. Adami, N. Wei, K. Keyomarsi and S. J. Elledge (1993) The p21 Cdk-Interacting protein Cip1 is a potent inhibitor of G1 cyclin-dependent kinases. *Cell* 75:805–816.

Helps, N. R., A. J. Street, S. J. Elledge and P. T. W. Cohen (1994) Cloning of the complete coding region for human protein phosphatase inhibitor 2 using the two hybrid system and expressing inhibitor 2 in *E. coli. FEBS Lett.* 340:93–98.

Hill, C. W. and B. W. Harnish (1982) Inversions between ribosomal RNA genes of *Escherichia coli. Proc. Natl. Acad. Sci. USA* 78:7069–7072.

Hoeffler, J. P., N. Bilir, T Marcell, K. Schneider, J. C. Dunkelberg, S. M. Jackson (1994) Isolation of single chain variable domains with high affinity antigen- binding characteristics using the two-hybrid system in yeast. *J. Cell Biochem.* (1994) Suppl. 18D, 190.

Johnson, M. and R. W. Davis (1984) Sequences that regulate the divergent GAL1–GAL10 promoter in *Saccharomyces cerevisiae. Molec. Cell. Biol.* 4:1440–1448.

Kalpana, G. V., S. Marmon, W. Wang, G. R. Crabtree and S. P. Goff (1994) Binding and stimulation of HIV-1 integrase by a human homolog of yeast transcription factor SNF5. *Science* 266:2002–2006.

Keegan, L., G. Gill and M. Ptashne (1986) Separation of DNA binding from the transcription-activating function of a eucaryotic regulatory protein. *Science* 231:699–704.

Klein, R. D. and L. L. Roof (1989a) Isolation of a gene from *Schwanniomyces occidentalis* which complements a ura3 mutation in *Saccharomyces cerevisiae. Curr. Genet.* 13:29–35.

Klein, R. D., R. A. Poorman, M. A. Favreau, M. H. Shea, N. T. Hatzenbuhler and S. C. Nulf (1989b) Cloning and sequence analysis of the gene encoding invertase from the yeast *Schwanniomyces occidentalis. Curr. Genet.* 16:145–152.

Klein, R. D. and T. G. Geary (1992) Method of identifying compounds useful as antiparasitic drugs. U.S. Pat. No. 5,079,143, issued, Jan. 7, 1992.

Klopotowski, T. and A. Wiater (1965) Synergism of amitrole and phosphate on the inhibition of the yeast imidazole glycerol phosphate dehydratase. *Arch. Biochem. Biophys.* 112:562–566.

Le Douarin, B., B. Pierrat, E. Vom Baur, P Chambon, R. Losson (1995) A new version of the two-hybrid assay for detection of protein-protein interactions. Human estrogen receptor DNA-binding domain and RAR-alpha receptor DEF region fusion protein expression in yeast, URA3 reporter gene. *Nucleic Acids Res.* 23: 5, 876–78.

Li, B. and S. Fields (1993) Identification of mutations in p53 that affect its binding to SV40 large T antigen by using the yeast two-hybrid system. *FASEB J.* 7:957–963.

Lorch, Y. and R. D. Kornberg (1984) A region flanking the GAL7 gene binding site for GAL4 protein as upstream activating sequences in yeast. *J. Mol. Biol.* 186:821–824.

Luban, J., K. L. Bossolt, E. K. Franke, G. V. Kalpana and S. P. Goff (1993) Human immunodeficiency virus type 1 Gag protein binds to cyclophilins A and B. *Cell* 73:1067–1078.

Ma, J. and M. Ptashne (1987) Deletion analysis of GAL4 defines two transcriptional activating segments. *Cell* 48:847–853.

Marszalek, J. and J. M. Kaguni (1994) DnaA protein directs the binding of DnaB protein in initiation of DNA replication in *Escherichia coli*. *J. Biol. Chem.* 269:4883–4890.

McHenry, C. (1992) DNA replication. In: Emerging Targets in Antibacterial and Antifungal Chemotherapy, eds. J. A. Sutcliffe and H. H. Georgopapadakou, Chapman & Hall, N.Y., pp. 37–67.

Morin, P. J., G. S. Subramanian and T. D. Gilmore (1993) GAL4-$1_xB_\alpha$ and GAL4-$1_xB_\gamma$ activate transcription by different mechanisms. *Nucleic Acids Res.* 21:2157–2163.

Paetkau, D. W., J. A. Riese, W. S. MacMorran, R. A. Woods and R. D. Gietz (1994) Interactions of the yeast RAD7 and SIR3 proteins: implications for DNA repair and chromatin structure. *Genes and Dev.* 8:2035–2045.

Rose, M. D., F. Winston and P. Hieter (1990) Methods in Yeast Genetics: A Laboratory Course Manual. Cold Spring Harbor Press, Cold Spring Harbor, N.Y.

Sambrook, J., E. F. Fritsch and T. Maniatis (1989) Molecular Cloning: A Laboratory Manual, 2nd ed. Cold Spring Harbor Laboratory Press, Cold Spring Harbor, N.Y.

Sato, T., M. Hanada, S. Bodrug, S. Irie, N. Iwama, L. H. Boise, C. B. Thompson, E. Golemis, L. Fong, H-G. Wang and J. C. Reed (1994) Interactions among members of the Bcl-2 protein family analyzed with a yeast two-hybrid system. *Proc. Natl. Acad. Sci USA* 91:9238–9242.

Spaargaren, M. and J. R. Bischoff (1994) Identification of the guanine nucleotide dissociation stimulator for Ral as a putative molecule of R-ras,H-ras,K- ras, and Rap. *Proc. Natl. Acad. Sci. USA* 91:12609–12613.

Stukenberg, P. T., J. Turner and M. O'Donnell (1994) An explanation for lagging strand replication: polymerase hopping among DNA sliding clamps. *Cell* 78:877–887.

Tougu, K., Peng, H. and Marians, K. J. (1994) Identification of a domain of *Escherichia coli* primase required for functional interaction with the DnaB helicase at the replication fork. *J. Biol. Chem.* 269: 4675–4682.

Vojtek, A. B., S. M. Hollenberg and J. A. Cooper (1993) Mammalian Ras interacts directly with the serine/threonine kinase Raf. *Cell* 74: 205–214.

Wickner, S. and J. Hurwitz (1975) Interaction of *Escherichia coli* dnaB and dnaC (D) gene products in vitro. *Proc. Natl. Acad. Sci. USA* 72: 921–925.

Yang M., S. Wu, and S. Fields, (1995) Protein-peptide interactions analyzed with the yeast two-hybrid system. A peptide library screening using the Sacccharomyces cerevisiae 2-hybrid system for analysis of retinoblastoma protein-peptide interaction. Nucleic Acids Res. 23: 7, 1152–56.

Ye, Z. S. and D. Baltimore (1994) Binding of the Vav to Grb2 through dimerization of Src homology 3 domains. *Proc. Natl. Acad. Sci. USA* 91: 12629–12633.

Yeung, K. C., J. A. Inostroza, F. H. Mermelstein, C. Kannabiran and D. Reinberg (1994) Structure-function analysis of the TBP-binding protein $Dr_1$ reveals a mechanism for repression of class II gene transcription. *Genes and Dev.* 8: 2097–2109.

Zang, X-F., J. Settleman, J. M. Kyriakis, E. Takeuchi-Suzuki, S. J. Elledge, M. S. Marshall, J. T. Bruder, U. R. Rapp and J. Avruch (1993) Normal and oncogenic $p21^{ras}$ proteins bind to the amino-terminal regulatory domain of c-Raf-1. *Nature* 364: 308–313

The documents cited are incorporated herein by reference.

BACKGROUND

The yeast two-hybrid system is extremely useful for studying protein:protein interactions. See Chien et al., 1991; Fields and Sternglanz, 1994; Harper et al., 1993; Vojtek et al., 1993; Luban et al., 1993; Li and Fields, 1993; Zang et al, 1993; Golemis and Brent, 1992; Sato et al., 1994; Coghlan et al., 1995; Kalpana et al., 1994; Helps et al., 1994; Yeung et al., 1994; Durfee et al., 1993; Paetkau et al., 1994; Spaargaren and Bischoff, 1994; Ye and Baltimore, 1994. (Full citations of references cited in this and subsequent sections may be found in the Information Disclosure, above.) Variations of the system are available for screening yeast phagemid (Harper et al., 1993; Elledge et al., 1991) or plasmid (Bartel et al., 1993a,b; Finley and Brent, 1994) cDNA libraries to clone interacting proteins, as well as for studying known protein pairs.

The success of the two-hybrid system relies upon the fact that the DNA binding and polymerase activation domains of many transcription factors, such as GAL4, can be separated and then rejoined to restore functionality (Morin et al., 1993).

Yeast strains with integrated copies of various reporter gene cassettes, such as GAL→LacZ, GAL→HIS3 or GAL→URA3 (Bartel et al., 1993a; Harper et al., 1993; Fields and Sternglantz, 1994) are co-transformed with two plasmids, each expressing a different fusion protein. One plasmid encodes a fusion between protein "X" and the DNA binding domain of, for example, the GAL4 yeast transcription activator (Brent and Ptashne, 1985; Ma and Ptashne, 1987; Keegan et al., 1986), while the other plasmid encodes a fusion between protein "Y" and the RNA polymerase activation domain of GAL4 (Keegan et al., 1986). The plasmids are transformed into a strain of the yeast that contains a reporter gene, such as lacZ, whose regulatory region contains GAL4 binding sites. If proteins X and Y interact, they reconstitute a functional GAL4 transcription activator protein by bringing the two GAL4 components into sufficient proximity to activate transcription.

Either hybrid protein alone must be unable to activate transcription of the reporter gene, the DNA-binding domain hybrid, because it does not provide an activation function, and the activation domain hybrid, because it cannot localize to the GAL4 binding sites. Interaction of the two test proteins reconstitutes the function of GAL4 and results in expression of the reporter gene.

The reporter gene cassettes consist of minimal promoters that contain the GAL4 DNA recognition site (Johnson and Davis, 1984; Lorch and Kornberg, 1984) cloned 5' to their TATA box. Transcription activation is scored by measuring either the expression of β-galactosidase or the growth of the transformants on minimal medium lacking the specific nutrient that permits auxotrophic selection for the transcription product, e.g., URA3 (uracil section) or HIS3 (histidine selection). See, Bartel et al., 1993a; Durfee et al., 1993; Fields and Sternglantz, 1994, and U.S. Pat. No. 5,283,173. These and all references cited in this application are hereby incorporated by reference.

The two-hybrid system offers a number of advantages for investigating protein interactions over older methods such as co-immunoprecipitation, crosslinking, and copurification through gradients or chromatographic columns. The biochemical methods have the major disadvantage that interacting proteins are generally known only as bands of a particular relative mobility on a polyacrylamide gel and to progress from these bands to cloned genes is often a difficult undertaking. The assay is performed in vivo, under conditions similar to those in which protein interactions normally occur. Purified target protein or antibody against this protein is not required to detect interactions. And the two-hybrid system appears to be more sensitive than co-immunoprecipitation.

There are no presently available methods for high volume screening for specific inhibitors of protein:protein interactions. This invention describes how to incorporate the two-hybrid system into an effective high volume screen for specific inhibitors of protein:protein interactions.

The documents cited in this section and all the sections below are incorporated by reference unless otherwise indicated.

SUMMARY OF THE INVENTION

This invention comprises a method for identifying useful compounds, especially antibacterial compounds comprising: a) the identification of a protein X::protein Y interaction of interest, (X::Y), where protein X and protein Y are proteins, different from each other, b) the cloning of one protein as a fusion to the DNA binding domain of the DNA that codes for a transcription activator protein, c) the cloning of the other protein as a fusion to the DNA activation domain of the DNA that codes for the same transcription activator protein, d) the maintaining of the two fusions as extrachromosomal elements in cells or the maintaining of the two fusions integrated in a yeast chromosome, where the extrachromosomal elements may be plasmids, e) the introduction of said fusions into a yeast screening strain, said yeast screening strain comprising one or more reporter gene cassette(s), said reporter gene cassette(s) comprising a reporter gene and comprising a DNA binding site specific to the DNA binding domain of the DNA coding region for said transcription activator protein, and said yeast screening strain is either dependent for growth upon the protein produced by said reporter gene, or where said yeast screening strain produces a protein by the reporter gene that is measurable, f) measuring said yeast screening strain for the expression of the reporter gene, g) selecting compounds that inhibit the expression of the reporter gene, h) measuring said selected compounds that inhibit the expression of the reporter gene in a yeast testing strain, said yeast testing strain being isogenic with said yeast screening strain, and comprising a protein pair, protein A::protein B, where protein A and protein B, are proteins, different from each other, and where protein(s) A and protein(s) B are different from protein(s) X and protein (s) Y, and where protein pair, protein A::protein B are required by said yeast testing strain in order to activate said reporter gene and where said yeast testing strain is either dependent for growth upon the protein produced by said reporter gene, or where said yeast testing strain produces a protein by the reporter gene that is measurable, i) selecting compounds that inhibit the growth of the screening strain but do not either: inhibit the growth of the testing strain or inhibit the measurable reporter gene.

More particularly, in one embodiment of the invention we describe a high volume screen where protein X is DnaB, the protein coded for by dnaB and where protein Y is DnaA, the protein coded for by dnaA (B::A); or where protein X is DnaB, the protein coded for by dnaB and where protein Y is DnaB, the protein coded for by dnaB (B::B); or where protein X is DnaB, the protein coded for by dnaB and where protein Y is DnaC, the protein coded for by dnaC (B::C); or where protein X is DnaB, the protein coded for by dnaB and where protein Y is DnaG, the protein coded for by dnaG (B::G).

In one embodiment of the invention the reporter gene is selected from a nutritional marker(s), or a measurable enzyme(s) integrated into the genome of a yeast or carried on an extrachromosomal element. The reporter gene may be selected from a nutritional marker that is HIS3 or URA3, or the reporter gene is selected from a measurable enzyme selected from, beta-galactosidase, beta- lactamase, luciferase, Green Florescent Protein, or chloramphenicol acetyl transferase (CAT). Any reporter gene that confers a growth related or metabolic activation phenotype is suitable for use with the system described herein.

The yeast screening strains may be selected from yeast cells viable in a selective media because the activation transcription of a reporter gene supplies a functional gene product necessary for cell growth. Examples of the yeast screening strains that are useful are described in Table 1. Table 1 provides a few examples only and is not an exhaustive or even a complete list of possible yeast screening strains.

Another embodiment of the invention describes a high volume screen that has multiple targets. This multi-target version of the two hybrid yeast assay adds a powerful dimension to the overall invention.

The multiple target system, MTS, or multiple target assay, MTA, comprises a method for identifying useful compounds comprising: a) the identification of 1 to 20 protein::protein interactions of interest, where the protein::protein interactions are indicated X::Y, where protein(s) X and protein(s) Y interact with each other at the cellular level, where the protein(s) X and protein(s) Y may be the same or different proteins, b) the cloning of one set of proteins, either X or Y, as fusions, or as a set of fusions, to the DNA binding domain of the DNA that codes for a transcription activator protein, c) the cloning of the other set of proteins, either X or Y, as fusions, or as a set of fusions, to the DNA activation domain of the DNA that codes for a transcription activator protein, d) the maintaining of the sets of fusions as extrachromosomal elements in cells or the maintaining of the sets of fusions integrated in a yeast chromosome, where the extrachromosomal elements may be plasmids, e) the introduction of said sets of fusions into several yeast screening strains, said yeast screening strains comprising one or more reporter gene cassette(s), said reporter gene cassette(s) comprising a reporter gene and comprising a DNA binding site specific to the DNA binding domain of the DNA coding region for said transcription activator protein, and said yeast screening strains are: a) dependent for growth upon the protein produced by said reporter gene, or b) where said yeast screening strains produces a protein by the reporter gene that is measurable, or c) where the reporter gene expressed by said yeast screening strains produces a product that converts a substance that is non-toxic to the yeast screening strain into a substance that is toxic to the yeast screening strain, f) growing the yeast in the presence of test compounds, where the test compounds are the compounds to be assayed, and a) growing the yeast in selective medium, where the medium contains material needed for growth; or b) growing the strains, where the strains produce a measurable protein; or c) growing the strains, where the medium contains a non-toxic compound that can be converted by the product of the reporter gene into a substance that is toxic to the yeast screening strain, g) selecting compounds that inhibit the expression of the reporter gene, h) identifying which yeast strains: a) are dependent upon the material needed for growth, b) produce a measurable protein or c) show growth inhibition; when exposed to selected compounds.

The preferred MTS system uses the "toxic product" variation. This is the method described above where (in part e) the reporter gene expressed by said yeast screening strains produces a product that converts a substance that is non-toxic to the yeast screening strain into a substance that is toxic to the yeast screening strain and (in part f) where the medium contains a non-toxic compound that can be converted by the product of the reporter gene into a substance that is toxic to the yeast screening strain, and (in part h) where the strains show growth inhibition when the yeast are exposed to selected compounds.

A preferred non-toxic compound is 5' Fluoro-orotic acid (FOA). This system may also be useful for identifying useful antibacterial compounds. The X::Y proteins include any combination of the following: DnaB::DnaA; DnaB::DnaB; DnaB::DnaC; DnaB::DnaG. The reporter gene may be selected from a nutritional marker(s), or a measurable enzyme(s) integrated into the genome of a yeast or carried on an extrachromosomal element. The reporter gene may be selected from a nutritional marker that is HIS3 or URA3, or where the reporter gene is selected from a measurable enzyme selected from, beta-galactosidase, beta-lactamase, luciferase, Green Florescent Protein, or chloramphenicol acetyl transferase (CAT). The yeast screening strains may be selected from yeast cells viable in a selective media because the activation transcription of a reporter gene supplies a functional gene product necessary for cell growth. The yeast screening strains may be selected from the yeast described in Table 1.

This invention may be useful for identifying inhibitors of specific prokaryotic/eukaryotic protein:protein interactions. The specific prokaryotic/eukaryotic protein:protein interactions may involve any of the Bacterial Attachment Factors, Bacterial Virulance Factors or Bacterial Protein Toxins.

Figure 1:
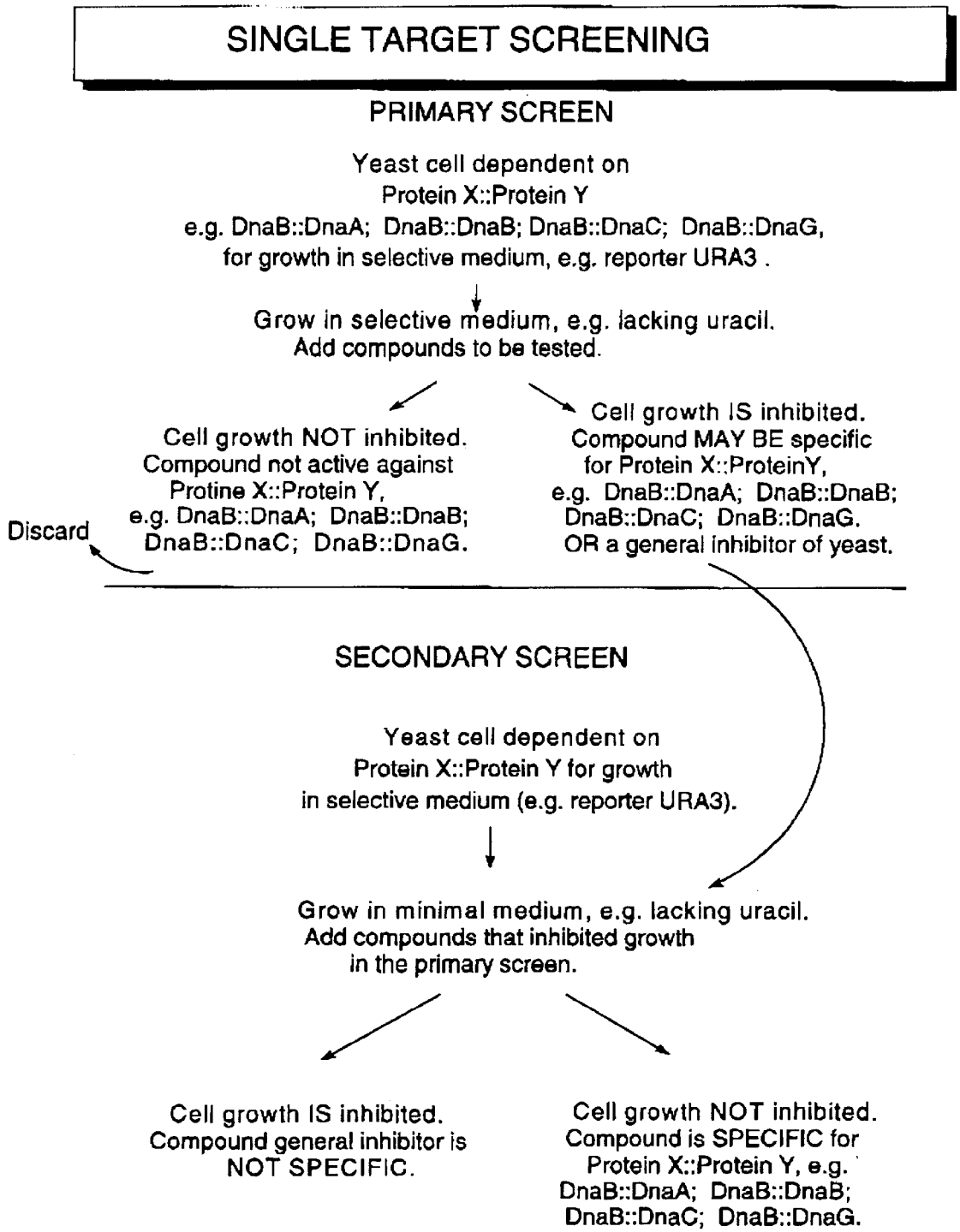
FIG. 1 provides a summary of the experimental strategy for demonstrating the interaction of DnaB and DnaA; DnaB and DnaB; DnaB and DnaC; and DnaB and DnaG.

ADDITIONAL DESCRIPTION OF THE INVENTION AND DESCRIPTION OF THE PREFERRED EMBODIMENT(S)

Definitions

Reference to DNA replication proteins will usually have a capitol "D" in the abbreviation "Dna" and reference to DNA genes will usually have a lower case "d" in the abbreviation "dna."

activation domain (or transcription activation domain). That portion of a transcription activator protein that interacts with RNA Polymerase and or associated proteins that enable transcription to occur.

arrow. "→" Arrow indicating direction of transcription or that a given promoter is driving transcription of a reporter gene.

DNA binding domain. That portion of a transcription activator protein that binds a particular DNA sequence.

drug target. The site of interaction of a specific compound. The drug target can be a distinct molecular entity or metabolic process within the organism affected by the compound. In this description the drug target represents a specific biological mechanism that is selected for disruption; thus, the process used to identify compounds active against the drug target is referred to as a "mechanism-based screen."

genotype. The genetic constitution of an individual including all alleles at a given locus or loci.

isogenic. Two organisms related by a common origin and sharing identical genotypes., with the exception of a single genetic difference that distinguishes the two.

oriC-dependent. Refers to prokaryotic DNA replication that initiates at a defined and unique origin of replication (oriC) contained on a given replicon.

phenotype. The entire physical, biochemical and physiological makeup of an organism or all traits of an organism as determined genetically and environmentally.

promoter. Segment of DNA where RNA polymerase binds and initiates transcription.

minimal promoter. A promoter that has been modified by removal of nucleotide sequences critical for the initial interaction of RNA polymerase with the promoter. The nucleotide sequences removed from the minimal promoter are responsible for the binding of transcription factors which place RNA polymerase and associated proteins in correct proximity with the DNA to be transcribed. RNA polymerase cannot initiate transcription at a minimal promoter unless binding sites for transcription activator proteins are restored.

protein::protein. Indicates a protein binding pair.

reporter gene. Gene whose product is used as an indication of transcription activity. Such as a gene that codes for a protein that permits growth in nutrient deficient medium like: HIS3 or URA3; or an enzyme whose activity is easily measured such as: β galactosidase, beta-lactamase, Green Fluorescent Protein, lucerferase, or chloramphenicol acetyl transferase (CAT).

reporter gene cassette(s). A segment of DNA, that can be transferred as a unit, containing a reporter gene and DNA sequences essential for its expression. essential sequences may include a promoter (a sequence of DNA where RNA Polymerase binds and initiates transcription), transcription termination sequences where transcription is terminated and transcription activation sites (DNA sequences that are recognized by proteins that regulate transcription).

replicon. A covalently closed circular DNA molecule capable of self-replication.

screen, primary or primary screen. Initial test of a library of compounds versus a specific drug target.

screen, secondary or secondary screen. A test or screen in addition to the primary screen to determine the drug target specificity of compounds identified as "hits" or actives in a primary screen.

screenable phenotype. A trait or traits of an organism that result from expression of a given drug target. The expression of the drug target should result in an easily scored or assayed phenotype and, if appropriate, should be adaptable to a high volume drug screen.

screening yeast. Yeast strain that contains a specific drug target and which is used for a first round or primary screen of compounds or materials that affect the drug target. he screening yeast is designed such that a compound that interacts with the drug target results in a phenotype or biochemical process that can be easily measured.

tester yeast. Yeast strain used in secondary assay to test the compounds identified in the primary screen as specific for the drug target.

two-hybrid yeast system. The two-hybrid system is a genetic method that uses transcriptional activity as a measure of protein::protein interaction. It relies on the modular nature of many site-specific transcriptional activators, which consist of a DNA-binding domain and a transcriptional activation domain. The DNA binding- domain serves to target the activator to the specific genes that will be expressed and the activation domain contacts other proteins of the transcriptional machinery to enable transcription to occur. The two-hybrid system is based on the observation that the two domains of the activator need not be covalently linked and can be brought together by the interaction of any two proteins. The application of this system requires that two hybrids be constructed: a DNA-binding domain fused to some protein, , and a transcription activation domain fused to some protein, . These two hybrids are expressed in a cell containing one or more reporter genes. If the X and Y proteins interact, they create a functional activator by bringing the activation domain into close proximity with the DNA-binding domain. This can be detected by expression of the reporter genes. While the assay has been generally performed in yeast cells, it works similarly in mammalian cells and should be applicable to any other eucaryotic cells. See, Phizicky, E. M. and S. Fields (1995) Protein-Protein Interactions: Methods for detection and analysis. Microbiological Reviews. 59:94–123, 105.

DEFINITIONS AND ABBREVIATED OR SHORTENED TERMS AND EXPRESSIONS

DnaA. Protein product of the *E.coli* dnaA gene. DnaA is a key component of bacterial DNA replication. DnaA binds directly to the origin of DNA replication (oriC) forming a complex exposing single stranded AT rich segments of DNA. The complex directs the DnaC-mediated delivery of the DnaB helicase to these exposed single stranded DNA sequences.

DnaB. Protein product of the *E.coli* dnaB gene. DnaB is a helicase and a key component of the bacterial chromosome DNA replication complex that unwinds duplex DNA. It has additional properties including DNA-dependent ATPase activity, binding of NTPs, and binding of single-stranded DNA.

DnaC. Protein product of the *E.coli* dnaC gene. One monomer of DnaC interacts with each subunit of the DnaB hexamer. This complex is delivered to the forming replication complex where DnaB interacts with other proteins, releasing DnaC.

DnaG. Protein product of the *E. coli* dnaG gene. A primase which synthesizes the short RNA primers that are required to initiate synthesis of the DNA (Okazaki) fragments that make up the nascent lagging strand DNA during DNA replication. A domain of the DnaG primase interacts with DnaB. This interaction with DnaB attracts DnaG to the DNA replication fork.

GAL. General designation for genes or the promoters of genes involved in galactose metabolism in the yeast *S. cerevisiae*. In the case of GAL promoters, here it refers to promoters regulated by the Gal4 protein.

Gal4. The gene product of the *S.cerevisiae* GAL4 gene. Gal4 is a transcription activator for genes involved in galactose metabolism, namely GAL1 and GAL10.

GAL→LacZ. *E.coli* β-galactosidase reporter gene expression, under control of a GAL (usually minimal) promoter containing the Gal4 DNA binding site.

GAL1→LacZ. As above, using intact promoter from the yeast GAL1 gene containing the GAL4 DNA binding sequence.

GAL→URA3 or HIS3. Gal-based reporter cassette, with yeast gene URA3 or HIS3 as reporter.

his. Yeast cell requiring histidine for growth.

HIS3. Yeast gene encoding imidazoleglycerol-P dehydratase.

his3. Mutated HIS3 gene.

LacZ. The product of the *E.coli* lacZ gene encoding the enzyme β-galactosidase, commonly used as a reporter for transcription activation studies.

leu. Yeast cell requiring leucine for growth.

LEU2. Yeast gene encoding β-IPM dehydrogenase.

leu2. Mutated LEU2 gene.

ura. Yeast cell requiring uracil for growth.

URA3. Yeast gene encoding orotidine-5'-phosphate decarboxylase.

ura3. Mutated URA3 gene.

The system described here is also expected to work well with many different protein complexes.

The adaptation of the two-hybrid system disclosed herein presents an opportunity for high volume screening for specific inhibitors of protein:protein interactions. The ability to screen relies upon the fact that the recombinant yeast is dependent on a functional interaction for survival in the absence of a particular nutrient.

For example, a transformed yeast could be made dependent on the expression of the HIS3 or URA3 auxotrophic marker in the absence of histidine or uracil, respectively. Investigation is then made into, for example, the DnaB:DnaB, or DnaB:DnaC, DnaB:DnaG or DnaB:DnaA complex. Inhibition of the DnaB:DnaB, the DnaB:DnaG interaction, the DnaB:DnaC or the DnaB:DnaA interaction would block formation of the functionally reconstituted GAL4 transcription activator, preventing cell growth in the absence of the selective nutrient.

One strategy for a high volume screen based on differential nutrient viability has been described (Klein and Geary, 1992). This invention describes a different screen that includes aspects of the nutrient viability screen described in U.S. Pat. No. 5,079,143, incorporated by reference. Here we present a novel high volume screen based on a combination of either differential nutrient viability or expression of a reporter gene and the two-hybrid system.

Either hybrid protein alone must be unable to activate transcription of the reporter gene, the DNA-binding domain hybrid, because it does not provide a transcription activation function, and the activation domain hybrid, because it cannot bind to the GAL4 DNA binding sequence. Interaction of the two test proteins reconstitutes the function of GAL4 and results in expression of the reporter gene.

The reporter gene may be any gene that confers a growth related or metabolic activation phenotype. The reporter gene cassettes consist of minimal promoters that contain the GAL4 DNA recognition site(s) (Johnson and Davis, 1984; Lorch and Kornberg, 1984) cloned 5' to their TATA box. Transcription activation is scored by measuring either the expression of reporter gene, such as β-galactosidase, or reporter genes that permit the growth of the transformants on minimal medium lacking the specific nutrient that permits auxotrophic selection for the transcription product, e.g., URA3 (uracil section) or HIS3 (histidine selection) (Bartel et al., 1993a; Durfee et al., 1993; Fields and Sternglantz, 1994).

To control for the possibility that proteins X-Y act as transcription activators for DNA sequences within the reporter cassettes, different reporter genes and cassettes are tested. These cassettes contain promoters from GAL1 or CYC1 and the reporter genes mentioned above (Feilotter et al., 1994; Bartel et al., 1993b). To score X-Y interactions as "positive," specific transcription activation must be demonstrated among this collection of reporter cassettes, requiring the co-transformation of several different yeast strains with plasmids expressing the hybrid protein pairs.

A protein::protein (X:Y) interaction of interest is first identified. The interacting proteins will be designated protein X and protein Y for the sake of discussion. One protein, protein X, is cloned as a fusion to the DNA binding domain of a transcription activator, such as Gal4. The other protein, protein Y, is cloned as a fusion to the activation domain of the transcription activator protein, such as Gal4. These protein fusions are maintained on plasmids known as fusion plasmids, or fusion protein plasmids.

The fusion protein plasmids are simultaneously introduced into a yeast strain (ie, the screening strain) that contains a reporter gene cassette(s); the promoter for the reporter gene cassette carries a DNA binding site specific to the DNA binding domain of the transcription activator being used. The screening strain is tested for the expression of the reporter gene, which could be a gene that permits growth on minimal medium such as HIS3, URA3 or some easily assayed enzyme such as β-galactosidase. For example, if URA3 is the reporter, the screening strain can be grown on medium lacking uracil.

To perform the primary screen, compounds are added to test wells containing the screening strain; putative "hits," or active compounds, are identified by their ability to inhibit cell growth. Compounds that inhibit growth of the screening strain might be general toxins or metabolic inhibitors; alternatively, the active hits might be specific inhibitors of the protein X::protein Y interaction. All active compounds should therefore be tested in a second isogenic yeast strain (ie, the tester strain) that is dependent on the interaction of a distinct protein pair (protein A::protein B) to activate the reporter gene.

If active compounds inhibit growth of the tester strain, they must target metabolic elements common to the two organisms; however, if the active compounds do not inhibit tester strain growth, then they must be affecting a molecular component unique to the screening strain. Since the strains are isogenic except for the identity of the interacting protein pairs, compounds that only inhibit growth of the screening strain must be affecting the interaction between protein X and protein Y.

This invention comprises the yeast and other two-hybrid systems and it discloses novel assays for inhibitors of protein:protein interactions such as the molecular interactions within a bacterial system and or interactions between bacteria and their eukaryotic hosts. Examples of protein-:protein interactions among bacterial systems are: the DnaB::DnaA complex, the DnaB::DnaB complex, the DnaB::DnaC complex, the DnaB::DnaG complex and the DnaG::DnaA complex.

In addition to creating a screen that identifies compounds that selectively interact with a single specific protein pair or pairs. One embodiment of this invention comprises a process for identifying many different interactions between protein pairs at once. This multiple target approach, or "Multiple Target Screening," or "MTS" can produce considerable savings of time, effort and reagents.

Multiple Target Screening (MTS). There are at least two possible approaches for an MTS strategy. The preferred approach is to use reporter genes that modify a drug or compound that in turn is toxic for the yeast cell. The protein:protein interaction would activate a given enzyme that would modify a specific compound into a metabolite that was toxic. Blocking the interaction of the protein:protein pair would block expression of the reporter gene which would mean that the compound would not be converted into a toxin. The absence of the toxin would permit the yeast cell to grow. In a single well containing a number of yeast strains dependent on different protein:protein pairs only the yeasts not making the reporter gene would grow. Such growth could be measured by viability dyes, incorporation of a labeled metabolite or even looking at the increase in the number of living cells by some optical means.

Figure 2:
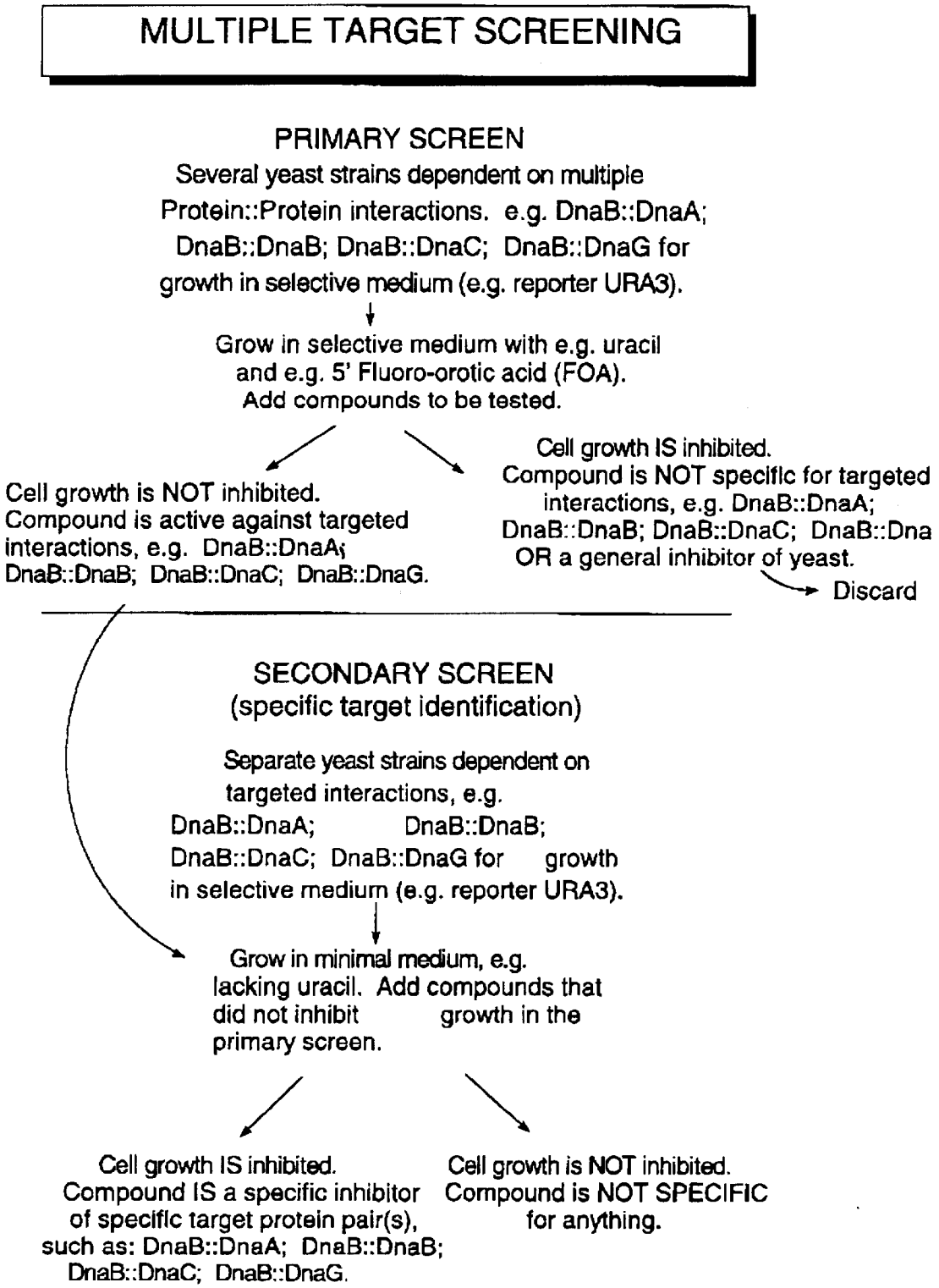
FIG. 2 provides a summary of the strategy for a Multiple Target Screening System.

An example of the MTS system is provided in FIG. 2. Comparing the single system to the multiple target system shows that both systems use two stages, or screens. With the single target screen the evaluator of the first stage, or primary screen, is looking for cell growth that IS inhibited following addition of the test compounds. This inhibition could be due to the compound affecting the protein::protein pair or it could be a general inhibitor of yeast. These two possibilities are distinguished in the second stage, or secondary screen. In the second stage a yeast strain dependent on a different protein::protein pair for growth is tested with the compounds identified as inhibitors in the first strain. The yeast strains that are used for both strains are identical (isogenic) except for the presence of a different protein::protein pair which permits growth in a selective medium. If the compound inhibits the second strain it must be inhibiting something that both strains have in common, and thus is a general inhibitor. IF the compound does NOT inhibit the strain used in the secondary screen but DOES inhibit the strain used in the primary screen the compound must be effecting the protein::protein pair of the first strain which is the ONLY difference between the strains.

With the Multiple Target Screen, there are also two stages or screens but they differs from the Single Target Screen. In the Multiple Target Screen the first stage, or primary screen, uses several strains of yeast with EACH strain dependent for growth on a different protein::protein interaction. These strains are placed together in the same well of a microtiter dish, tube or vial. The protein::protein pair interaction(s) allow transcription of a reporter gene as in the Single Target Screen; however, added to the medium is a compound that the reporter gene converts into a molecule toxic to the yeast. Thus, the protein protein interaction results in the death of the yeast cell if the compound is present.

FIG. 2 provides an example using 5-fluoro-orotic acid (5'-FOA). The reporter gene URA3 converts this into a toxic compound. If the protein::protein interaction is blocked URA3 is not made and 5'-FOA is not converted the cell will grow (uracil is added to the medium to supplement the ura3 mutation). Thus in the primary stage the mixture of cells are exposed to the test compounds and FOA with uracil added. If the cell(s) are not inhibited, i.e. they grow, the test compound is affecting a protein::protein interaction or blocking the conversion of 5'-FOA to a toxic substance and these compounds advance to the second stage. If the cells are inhibited the compound is either a general inhibitor of all of the yeast strains or it has no effect on any of the protein::protein interactions. The secondary screen is similar to the primary screen of the Single Target Screen, only in the secondary screen of the MIS the compound identified in the primary screen is tested against each of the individual yeast strains dependent on different protein::protein interactions for the expression of the reporter gene and cell growth. Cells are grown in medium requiring the expression of the reporter gene. If they ARE INHIBITED the compound must be specific for that strain's protein::protein interaction, if they are NOT INHIBITED then the compound was affecting something other than the protein::protein interaction in the primary assay. FIG. 2 provides only 4 examples of hundreds of possible protein::protein interactions. The screen disclosed herein could easily accommodate any combination of one to 20 targets. One to 10 target interactions would be more common and evaluating 5 or fewer separate target interactions "at once" or in the MTS mode would be very easy and convenient.

Further descriptions of reporter genes that could be used in this "toxic gene" version of MTS, and examples of the system in operation are provided below.

An alternative system of using this invention in an MTS mode would be to identify a compound that selectively interacted with a single specific protein pair or pairs. Reporter gene expression would have to be blocked in all of the strains being tested by the interaction of the two target proteins. This could be accomplished by the reporter gene (Gene A) being, for example, a gene product that would block the transcription of another gene (Gene B) which, for example, would be required for growth on selective medium. In this system blocking the target protein:protein interaction would diminish the expression of gene A, the transcription regulator of gene B, which in turn would "derepress" expression of the measurable reporter gene (gene B). In this system, a compound that blocked the interaction of the target proteins, would in effect "turn off" expression of a gene product that repressed the expression of a easily measurable reporter gene. If the reporter gene was essential for growth on selective medium, the compound that blocked the interaction of the target proteins would result in cell growth.

Without further description it is expected that one reasonably skilled in the art should be able to practice this invention. To further illustrate the invention two examples of particular protein-protein interactions and a high volume screen for inhibitors of those interactions are provided. The examples provided should not be used to limit the invention in any manner.

A general procedure for identifying drug targets from specific proteins: First, the target genes are identified and isolated by PCR or its equivalent, then an interaction between the two genes is demonstrated, and finally a screening strategy for the protein interaction is executed.

IDENTIFICATION OF SPECIFIC PROKARYOTIC/EUKARYOTIC PROTEIN:PROTEIN INTERACTIONS

The yeast two hybrid system and screening strategy described above can be used to identify small molecule inhibitors of specific prokaryotic/eukaryotic protein:protein interactions. Such interactions are required for the successful establishment of an infection in a susceptible host; interference with such interactions would provide an effective therapeutic capable of blocking a given infection.

For this type of interaction one protein, such as protein X, corresponds to a prokaryotic protein and the second protein, such as protein Y corresponds to the specific eukaryotic protein with which it interacts. Examples of prokaryotic/eukaryotic interactions amenable to the above screening strategy include the following:

Bacterial Attachment Factors

Bacterial attachment factors include pili and nonfimbrial adhesions (P pili in uropathogenic *E. coli;* type I pili, CFAI and II antigens, bundle forming pili and longus pili in enterotoxigenic *E. coli;* GVVPQ fimbriae in enteroaggregative *E. coli;* BFP, EAF and intimin in enteropathogenic *E. coli;* type IV pili in *Neisseria gonorrhoea* and *Pseudomonas aeruginosa;* FHA antigen in *Bordatella pertussis;* and TCP and Acf antigens in *Vibrio cholera* are common examples) which bind to specific host glycoprotein receptors; nonfibrillar adhesion (protein F) of *Streptococcus pyogenes* that binds to the host protein fibronectin found on many cell surfaces; other adhesions of gram positive bacteria that have eukaryotic surface protein targets.

Bacterial Virulence Factors

Some bacterial virulence factors block proper functioning of the host immune system. Common examples include IgA proteases (*N. gonorrhoea*) and C5a peptidases (*Streptococcus pyogenes*); protein A (*Staphylococcus aureus*) and protein G (*Streptococcus pyogenes*) that bind the Fc portion of antibodies, preventing normal host recognition of the bacteria; protein SpH of *Streptococcus pyogenes*, which binds to host alpha$_2$-macroglobulin thereby inactivating this important host protease inhibitor; bacterial superantigens such as *Staphylococcus aureus* TSST-1 toxin, which binds directly to MHC class II antigens on antigen presenting cell surfaces.

Other bacterial virulence factors mediate entry of the bacterium into a susceptible host cell; common examples include the invasin (Inv) protein of *Yersinia pseudotuberculosis* which interacts directly with specific host cell B1-integrin moeities, triggering invasion, or internalin of *Listeria monocytogenes,* which interacts with macrophage complement receptor, or YadA of *yersinia enterocolitica* which interacts with host cell B1 integrins, laminin, and fibronectin. Other less will defined examples include Shigella invasins IpaB, IpaC, and IpaD, the Ail protein of *Yersinia enterocolitica,* Inv proteins of Salmonella, TiaA and TiaB of enterotoxigenic *E. coli,* Mip protein of *Legionella pneumophila,* and invasin homologues in enteropathogenic *E. coli.*

Some bacterial virulence factors interact with host cell actin. This interaction provides a motive force to internalized bacteria allowing their spread intracellularly and to other cells; common examples include the IcsA (or virG) protein of Shigella and the ActA protein of *Listeria monocytogenes*. Bacterial proteins that induce the rearrangement of host cell actin to facilitate attachment or uptake of the bacteria are also included, a common example being the intimin (eaeA) protein of enteropathogenic *E. coli.*

Bacterial Protein Toxins

Bacterial protein toxins, sometimes referred to as exotoxins, are compounds that interact with and inactivate host proteins. Common examples of bacterial protein toxins include A-B toxins such as diptheria toxin (*Clostridium diptheriae*) which inactivates eukaryotic elongation factor-2, or cholera toxin (*Vibrio cholerae*) which inactivates a host regulatory protein controlling cAMP levels and pertussis toxin (*Bordatella pertussis*). The B-chain of such toxins also recognizes particular host cell protein receptors, an example being the heparin-binding epidermal growth factor receptor for diptheria toxin B subunit. Host factors that activate toxin activity might also be targetted, an example being the FAS (factor activating exoenzyme S) protein which activates *Pseudomonas aeruginosa* exoS function.

Other types of prokaryotic/eukaryotic protein:protein interactions in addition to bacterial attachment factors, bacterial virulence factors, and bacterial protein toxins should be obvious to those skilled in the art. Additional protein-:protein interactions that fall within those three catagories should also be obvious.

In addition to prokaryotic/eukaryotic protein:protein interactions, this invention teaches the creation of high volume screens designed to detect and discover compounds that inhibit or interfere with the prokaryotic DNA replication complex.

The following procedure is a general one, it is merely for the ease of discussion and by way of example that dnaB, dnaC and dnaG genes and the proteins they code for are discussed.

THE PROKARYOTIC DNA REPLICATION COMPLEX

The prokaryotic DNA replication complex represents an attractive but largely unexplored family of targets for the discovery of new antibiotics. The size of the replisome (1.7 MDa) approaches that of the ribosome (Arai et al., 1981). Antibiotics that block translation are structurally diverse and they do not resemble substrates of the ribosome, it is likely that this invention will lead to novel structural classes of drugs that will be found that specifically block DNA replication.

Prokaryotics have essential biochemical processes many of which are amenable to analysis with a high volume screen of the type described here. Especially suitable for screening are processes involved with: proteosomes, translation, transcription, DNA replication, cell wall synthesis, gene regulation, cell division, protein transport, cellular motility, flagellum, chemotaxis, conjugation, and ribosomal activities.

These prokaryotic biochemical processes amenable to analysis should provide novel inhibitors that inhibit the following types of various prokaryotic organisms and/or their associated diseases.

Gram positive bacterial pathogens, include:

*Staphylococcus aureus, Staphylococcus epidermidis* (A, B, C biotypes), *Staphylococcus caseolyticus, Staphylococcus gallinarum, Staphylococcus haemolyticus, Staphylococcus hominis, Staphylococcus saprophyticus, Streptococcus agalactiae* (group B), *Streptococcus mutans/rattus, Streptococcus pneumoniae, Streptococcus pyogenes* (group A), *Streptococcus salivarius, Streptococcus sanguis, Streptococcus sobrinus, Actinomyces spps., Arthrobacter histidinolovorans, Corynebacterium diptheriae, Clostridium difficle, Clostridium spps., Enterococcus casseliflavus, Enterococcus durans, Enterococcus faecalis, Enterococcus faecium, Enterococcus gallinarum, Erysipelothrix rhusiopathiae, Fusobacterium spps., Listeria monocytogenes, Prevotella spps., Propionibacterium acnes, Porphyromonas gingivalis*

Gram negative bacterial pathogens, include:

*Acinetobacter calcoaceticus, Acinetobacter haemolyticus, Aeromonas hydrophila, Bordetella pertussis, Bordetella parapertussis, Bordetella bronchiseptica, Bacteroides fragilis, Bartonella bacilliformis, Brucella abortus, Brucella melitensis, Campylobacter fetus, Campylobacter jejuni, Chlamydia pneumoniae, Chlamydia psittaci, Chlamydia trachomatis, Citrobacter freundii, Coxiella burnetti, Edwardsiella tarda, Edwardsiella hoshinae, Enterobacter aerogenes, Enterobacter cloacae* (groups A and B), *Escherichia coli* (to include all pathogenic subtypes), *Ehrlicia spps., Francisella tularensis, Haemophilus actinomycetemcomitans, Haemophilus ducreyi, Haemophilus haemolyticus, Haemophilus influenzae, Haemophilus parahaemolyticus, Haemophilus parainfluenzae, Hafnia alvei, Helicobacter pylori, Kingella kingae, Klebsiella oxytoca, Klebsiella pneumoniae, Legionella pneumophila, Legionella spps., Morganella spps., Moraxella cattarhalis, Neisseria gonorrhoeae, Neisseria meningitidis, Plesiomonas shigelloides, Proteus mirabilis, Proteus penneri, Providencia spps., Pseudomonas aeruginosa, Pseudomonas species, Rickettsia prowazekii, Rickettsia rickettsii, Rickettsia tsutsugamushi, Rochalimaea spps.,* Salmonella subgroup 1 serotypes (to include *S. paratyphi* and *S. typhi*), Salmonella subgroups 2, 3a, 3b, 4, and 5, *Serratia marcesans, Serratia spps., Shigella boydii, Shigella flexneri, Shigella dysenteriae, Shigella sonnei, Yersinia enterocolitica, Yersinia pestis, Yersinia pseudotuberculosis, Vibrio cholerae, Vibrio vulnificus, Vibrio parahaemolyticus*

Mycobacterial species, include:

*Mycobacterium tuberculosis, Mycobacterium avium,* other Mycobacterium spps.

Mycoplasmas (or pleuropneumonia-like organisms), include:

*Mycoplasma genitalium, Mycoplasma pneumoniae,* other Mycoplasma spps.

Treponemataceae (spiral organisms), include:

*Borrelia burgdorferi,* other Borrelia species, Leptospira spps., *Treponema pallidum*

The DNA replication protein inhibitors, the new antibiotics, will most likely have little resemblance to either nucleotides or gyrase inhibitors (e.g., quinolones, coumarins), classes of compounds to which past replication inhibitor work has been mostly confined (McHenry, 1992).

Replication inhibitors have been sought using a cell-free oriC-dependent replication system (Demyan et al., 1993), targeting replisome function as a whole. A complementing approach would be to target key components of the replisome, such as DNA polymerase, primase or helicase.

The *E. coli* helicase protein, encoded by the dnaB gene, is a unique element of the replisome in that it participates in all three facets of DNA replication: initiation, elongation and termination (McHenry, 1992). DnaB helicase is required for primosome assembly and replication initiation. In this capacity, DnaB hexamer complexes with six monomers of DnaC protein and this complex is delivered to the pre-primosome structure composed of DnaA initiator protein bound to the oriC initiation site.

Recently it has been shown that DnaB directly interacts with DnaA in the primosome (Marszalek and Kagun, 1994). When complexed with DnaC protein, the ssDNA-dependent ATPase activity of DnaB is feeble; in the absence of DnaC, the ATPase activity of DnaB improves and is correlated with its function as a helicase that moves processively along the ssDNA to advance the replication fork. Thus, the balance of DnaB and DnaC in the cell is critical for the correct delivery and functioning of the helicase, to the extent that mutations in either component result in a "quick stop" phenotype (Allen and Kornberg, 1991).

Once loaded onto the template DNA, DnaB helicase interacts with a C- terminal domain of the elongation-specific protein DnaG primase (Tougu et al., 1994). This interaction is critical since it coordinates the synthesis of RNA Okazaki fragments on the lagging strand with the unwinding of the replication fork.

Finally, DnaB helicase is involved in termination of DNA replication. The terminator protein (Tus) functions to inhibit DNA translocation and unwinding activities of DnaB helicase, causing dissociation of helicase/ssDNA template and termination of DNA replication (Hiasa and Marians, 1992).

All of these protein:protein complexes are particularly adaptable to this invention. In particular, several avenues of attack are available to block specific DnaB interactions with other replisome proteins. The interaction of DnaB and DnaC is extremely well characterized (Wickner and Hurwitz, 1975).

Based on the demonstrable importance of the DnaB:DnaC interaction and the critical nature of the DnaB::DnaG interaction in bacterial DNA replication and the presumed conservation of structure of these proteins among bacteria, there is little doubt that inhibitors of either of these interactions can be developed into novel antibiotics. The yeast two-hybrid system offers an unprecedented opportunity to devise highly specific screens for compounds that disrupt or modify protein:protein interactions.

Isolation of dnaB, dnaC and dnaG genes by PCR:

The genes encoding proteins, such as DnaB, DnaG and DnaC, are cloned by a PCR-based strategy from *E.coli,* or other appropriate genomic DNA. PCR primers are designed with restriction sites such that the amplified DNA products, when cloned into the appropriate vectors, create in-frame fusions with either the DNA binding domain or activation domain of, for example, the Gal4 transcription activator. For example, a good restriction site for cloning dnaB into pAS2 is NdeI and BamHI; dnaC can be cloned into pACTII using XhoI and BamHI and DnaG can be cloned into pACTII using BamHI and EcoR1. Correct construction of the fusions, in this example pAS2-dnaB, pACTII-dnaC and pACTII-dnaG, should be confirmed by DNA sequence analysis.

DEMONSTRATING THE INTERACTION BETWEEN TWO PROTEINS SUCH AS DNAB AND DNAC

When fusion proteins interact they reconstitute a functional transcription activator protein, such as a functional Gal4 and a phenotype that can be measured by assessing the expression of a reporter gene. It is also possible that either fusion protein alone or the specific combination of fusion proteins results in activation of reporter gene expression by binding of one or both fusions to a nucleotide sequence other than GAL4 DNA binding site present in the reporter gene or promoter or an interaction of one of the fusion proteins with a protein present in the yeast cell that activates transcription of the reporter.

In order to demonstrate the specificity of the interaction between proteins such as, DnaB and DnaG or DnaB and DnaC, a series of transformation experiments are conducted to discount other possible explanations for expression of the reporter gene.

The plasmids pAS2-DnaB and pACTII-DnaC or pAS2-DnaB and pACTII- DnaG are introduced into yeast cells that contain various reporter and promoter expression cassettes; the plasmids are also introduced individually or paired with other fusion proteins. Table 1 summarizes a few yeast strains studied. Differences between these strains include: HIS3 reporter gene for Hf7c and Y190; URA3 for Y166; lacZ for Hf7c, Y190, Y166 and SFY526. All strains use the GAL1 promoter except for HF7c where lacZ is under control of the CYC1 promoter (which contains three copies of a 17 bp sequence corresponding to the minimal GAL4 DNA binding site). Expression of all reporter genes from these strains is required to confirm that the fusion proteins are specific for the GAL4 DNA binding site. Some of these data are summarized in Table 2.

In these experiments only cells containing both pAS2-DnaB and pACTII- DnaC activated transcription in the strains listed in Table 1. Transcription is not demonstrated when either fusion is introduced into these strains when paired with other heterologous fusion proteins. The data presented indicate that DnaB and DnaC, and DnaB and DnaG are specifically interacting in the yeast strains.

Creating the Screen

A screen for compounds that disrupt the interaction of target proteins such as, DnaB::DnaC or DnaB::DnaG would have the following components:

Screening strain. The strain should have a mutation in a specific gene resulting in its inability to grow in a selective medium. For example, the strain Y166 is ura3 and can only grow if uracil is present in the medium, or if the GAL--->URA3 reporter is activated by reconstitution of a functional GAL4 transcription activator through the interaction of two fusion proteins, in this case DnaB::DnaC or DnaB::DnaG. Thus, in selective medium lacking uracil, growth of the cell is dependent on the interaction of DnaB and DnaC or DnaB and DnaG. Strains possessing other reporters, such as HIS3 can be used. In addition, a reporter gene whose expression can be measured can also be used (e.g. lacZ). In one embodiment of the invention, the screening strain used in the primary screen may consist of a two-hybrid yeast containing pAS2-DnaB and pACTII-DnaC or the pair of pAS2-DnaB and pACTII-DnaG. Growth of the screening strain on selective medium must be dependent on the interaction of DnaB::DnaC or DnaB::DnaG.

Tester Strain. The tester strain is used in the secondary assay to confirm the specificity of any compounds that inhibit the growth of the screening strain in the primary screen. The tester strain is identical to the screening strain but instead of containing the protein::protein pair used in the screening strain, e.g. DnaB::DnaC or DnaB::DnaG, the growth of the tester strain on selective medium is dependent on the presence of a different pair of fusion proteins, such as murine p53::SV40 large T antigen. Thus, the only difference between the screening strain and tester strain is the specific protein::protein pair.

Screening strategy

The screening strain is grown in selective medium supplemented with the appropriate nutrient, see U.S. Pat. No. 5,079,143, or in this example, uracil. In one embodiment of the invention the cells are harvested and washed to remove all traces of exogenous nutrient or uracil. The cells are diluted in selective medium lacking uracil to a density of 25–200 cells per 100ul of medium. Wells of a 96 well microtiter dish are seeded with 100ul of resuspended cells. Test compounds or materials are added, approximately 5ul. The microtiter dish is incubated with mild shaking at 30° C. for sufficient time to permit cell growth. The microtiter plate is removed and cell growth tested by the addition of a viability dye (Alamar Blue). The degree of inhibition is determined by comparison to wells containing cells but no compound, wells containing only medium and wells containing cells plus an antimycotic. Rapidly metabolizing cells turn the purple dye pink, whereas the color of the dye remains unchanged if cell growth is seriously inhibited.

Suitable volumes, dilutions, dishes, suspensions and conditions will vary in amounts suitable for a variety of conditions that should be obvious to one ordinarily skilled in the art.

Compounds that inhibit cell growth could do so by being general toxins or by specifically blocking the reconstitution of the Gal4 transcription activator through interference with either the interaction of the target proteins or some element involved in transcription activation. To distinguish between these possibilities the compounds are reassayed versus the tester strain of yeast. This yeast is identical to that used in the primary assay with the exception that its growth in selective medium is dependent on a different fusion protein pair. In other words, the strains used in the primary and secondary assay are identical EXCEPT for the paired fusion proteins. Thus, the expression of the reporter gene in the tester strain is dependent on the interaction of a different protein pair.

In theory, a compound that inhibits the growth of both the screening yeast and the tester yeast must block a metabolic process both yeast have in common, i.e. all biochemical functions EXCEPT the fusion protein pairing. If the compound only inhibits the screening yeast and not the tester strain, that inhibition must be occurring at a site only present in the screening yeast but not the tester yeast. Since the only difference between the two yeasts is the fusion protein pairing then the site of interaction must involve the fusion protein pair of the screening strain.

A tester strain could be any fusion protein pairing, such as murine p53 and the SV40 Large T antigen. The assay is conducted and scored as described for the primary screen using the screening strain.

This screening system will work for a variety of versions of the two-hybrid system. Examples of possible alternative systems are DNA-binding domains from the yeast Gal4 protein, the *E.coli* LexA protein, see, Zervos A. S., J. Gyuris and R. Brent, "Mxi1, a protein that specifically interacts with Max to bind myc-Max recognition sites." (1993) Cell 72:223–232, with transcriptional activation domains from the Gal4 protein or the Herpes VP16 protein, see Dalton, S. and R. Treisman "Characterization of SAP-1, a protein recruited by serum response factor to the c-fos serum response element." (1992) *Cell* 68:597–612 and the human estrogen receptor DNA binding domain and RAR-alpha receptor DEF region, see, Le Douarin, B., B. Pierrat, E. Vom Baur, P Chambon, R. Losson (1995) A new version of the two-hybrid assay for detection of protein-protein interactions. Human estrogen receptor DNA- binding domain and RAR-alpha receptor DEF region fusion protein expression in yeast, URA3 reporter gene. *Nucleic Acids Res.* 23: 5, 876–78. Al cited documents are incorporated by reference.

Multiple Target Screening (MTS).

One embodiment of this invention comprises a process for identifying many different interactions between protein pairs at once. This multiple target approach, or "Multiple Target Screening," or "MTS" can produce considerable savings of time, effort and reagents.

Multiple Target Screening (MTS). There are at least two possible approaches for an MTS strategy.

One possible system of using this invention in an MTS fashion would be to identify a compound that selectively interacted with a single specific protein pair or pairs. Reporter gene expression would have to be blocked in all of the strains being tested by the interaction of the two target proteins. This could be accomplished by the reporter gene (Gene A) being, for example, a gene product that would block the transcription of another gene (Gene B) which, for example, would be required for growth on selective medium. In this system blocking the target protein:protein interaction would diminish the expression of gene A, the transcription regulator of gene B, which in turn would "derepress" expression of the measurable reporter gene (gene B). In this system, a compound that blocked the interaction of the target proteins, would in effect "turn off" expression of a gene product that repressed the expression of a easily measurable reporter gene. If the reporter gene was essential for growth on selective medium, the compound that blocked the interaction of the target proteins would result in cell growth.

The preferred MTS approach is to use reporter genes that modify a drug or compound that in turn is toxic for the yeast cell. The protein:protein interaction would activate a given enzyme that would modify a specific compound into a metabolite that was toxic. Blocking the interaction of the protein:protein pair would block expression of the reporter gene which would mean that the compound would not be converted into a toxin. The absence of the toxin would permit the yeast cell to grow. In a single well containing a number of yeast strains dependent on different protein:protein pairs only the yeasts not making the reporter gene would grow. Such growth could be measured by viability dyes, incorporation of a labeled metabolite or even looking at the number of life cells by some optical means.

Possible reporter genes that convert compounds into metabolic toxins are LYS2, LYS5, URA5 and URA3. This invention is not limited to any of these examples. Wild-type yeast convert alpha-aminoadipate (α-AA) to a toxic intermediate by the lysine metabolic pathway (Chattoo et al. Genetics 93:51–65 (1979) and Zaret and Sherman. J. Bacteriol. 162:579–583 (1985)) the genes specifically involved in the conversion are LYS2 and LYS5. 5-fluoro-orotic acid (5-FOA) is converted to 5-fluoro-orotidine monophosphate via conjugation to phosphoribosyl pyrophosphate which in turn is decarboxylated to 5-fluoro-uridine monophosphate (5FUMP). 5FUMP is converted to fluorodeoxyuridine, a potent inhibitor of thymidylate synthetase, which is toxic to the cell. Utilization of FOA can be blocked at mutations of two genes involved in the de novo synthesis of uridine, URA3 and URA5. Both are required for the conversion of 5-FOA to 5-FUMP. Mutants of URA3 and URA5 will grow in the presence of 5-FOA if uracil is provided in the growth medium (Boeke et al. Mol. Gen. Genet. 197:345–346.).

Once a well that exhibited growth was identified the contents of that well would be evaluated in a second screen where the yeast strains would be placed in separate wells, each well containing a different target protein::protein pair. Inhibition of cell growth in this second screen would indicate specific target protein pair inhibition. See FIG. 2.

BRIEF DESCRIPTION OF A MULTIPLE TARGET SCREEN (MTS)

Yeast strains dependent on the interaction of DnaB::DnaB; DnaB::DnaC; DnaB::DnaA; and DnaB::DnaG would be seeded to the wells of a microtiter dish. Compound would be added and preincubated for a time. Minimal medium lacking tryptophane, leucine and uracil would be added to the wells along with FOA, (fluoro- orotic acid) and uracil. If the compounds do not affect any of the protein::protein interactions the URA3 gene product converts FOA into 5-floruro uracil and these yeast cells die or are severely inhibited. If a compound does block or interfere with the interaction of one or more of the protein pairs (e.g. DnaB::DnaC and DnaB::DnaG) the URA3 gene product will not be made and FOA will not be converted into the toxin 5 fluoro- uracil and the cells will grow. Growth can be determined by absorbance spectroscopy or by a viability dye such as Alamar Blue, a metabolic viability stain or other methods that will distinguish living cells, growing cells etc. Partial inhibition of the protein::protein interaction should result in lowering the amount of the URA3 gene product, this partial inhibition can be measured by the incorporation of a labeled metabolite such as radio labeled uracil. A measure of increase of incorporation of the labeled uracil versus background (i.e.) cells that are not metabolizing will distinguish this partial inhibition.

Once cell growth is established then it can be determined which protein::protein pair was inhibited by testing each yeast strain separately in a second screen. See FIG. 2.

Without further description it is expected that one reasonably skilled in the art should be able to practice this invention. To further illustrate the invention one example of a particular protein-protein interaction and a high volume screen for inhibitors of that interaction is provided. This, and all other examples provided, should not be used to limit the invention in any manner.

BRIEF DESCRIPTION OF A HIGH VOLUME SCREEN FOR INHIBITORS OF THE DNAB:DNAC AND DNAB::DNAG INTERACTION

Protein:protein systems particularly adaptable to this invention are the interaction between DnaB::DnaC and DnaB::DnaG. A description of this invention adapted for screening inhibitors of the DnaB:DnaC interaction follows.

Two-hybrid dependent yeast cells are preferably grown in 96-well microtiter dishes in minimal medium lacking uracil (for strain Y166) or histidine (for strain HF7c). Compounds are added and the plates incubated for 24–48 hrs. Yeast replication and viability can be estimated by measuring incorporation of radiolabeled material or by monitoring color changes of the viability dye Alamar Blue.

Compounds that inhibit growth of the recombinant yeast are then tested for specificity. A secondary assay will eliminate compounds that have non-specific, general toxicity, inhibit GAL4 binding or activation or directly inhibit the reporter gene. This secondary assay would test primary positives against the same yeast strain, but dependent on a different two-hybrid pair (e.g., p53:SV40 large T antigen). The only difference between the primary and secondary screening strains is the paired proteins. Primary positive compounds that are inactive in the secondary screen must be specific for the DnaB:DnaC interaction.

Secondary positives can be further characterized by measuring their effects on the level of reporter gene expression, which is proportional to the degree of transcription activation. It has been demonstrated that weak protein:protein interactions (e.g., SNF1:SNF4) result in lower levels of β-galactosidase than do stronger interactions (p53:SV40 large T antigen, or calcineurin A:calcineurin B; Li and Fields, 1993; Harper et al., 1993; Fields and Sternglanz, 1994). Thus, the β-galactosidase assay can be used to assess the efficacy and potency of a compound that inhibits the target DnaB:DnaC interaction.

SPECIFIC EXAMPLES OF THE INVENTION

The following specific reagents and materials are illustrations and not limitations of the invention. Full citations to the references mentioned below can be found in the Information Disclosure.

Materials and Methods

Strains, Plasmids and Media

Some yeast strains are listed in Table 1. *E. coli* manipulations were in DH5α (Bethesda Research Laboratories, Bethesda, Md.). Media for yeast and bacterial selections and growth have been described previously (Klein et al., 1989a, b; Bartel et al., 1993a), as have plating and growth procedures (Rose et al., 1990). Incorporated by reference.

Two hybrid vector plasmids are pAS2 (containing the GAL4 DNA binding domain and TRP1 marker) and pACTII (containing the GAL4 activation domain and LEU2 marker). See, Durfee et al., 1993; Harper et al., 1993. Plasmids used as controls for two-hybrid interactions include: pSE1111, containing the *S. cerevisiae* SNF4 gene (Fields and Song, 1989) fused to the activation domain of GAL4 in the vector pACT, and pSE1112, containing the SNF4 interacting protein SNF1 gene product (Fields and Song, 1989) fused to the DNA binding domain of GAL4 in the vector pAS. Alternative control plasmids were pVA3, expressing amino acids 72–390 of murine p53 fused to the GAL4-DNA binding domain in the vector pGBT9, and pTD1, expressing a fusion of amino acids 84–708 of the SV40 large T antigen to the activation domain of GAL4 in the vector pGAD3F. Both plasmids have been described. See, S. Fields, State University of New York (SUNY), Stony Brook, N.Y., (Li and Fields, 1993). Incorporated by reference.

DNA Manipulations

DNA manipulations, including nucleotide sequence analysis, restriction enzyme digestions, agarose gel electrophoresis, isolation and purification of DNA restriction fragments and PCR products and large and small scale plasmid isolations from yeast and bacteria, were performed as described previously (Klein et al., 1989a,b; Sambrook et al., 1989; Ausubel et al., 1994). PCR protocols were of standard design (Ausubel et al., 1994).

Bacterial and Yeast Transformations

Transformation of bacterial cells was performed by standard techniques (Ausubel et al., 1994). Transformation of yeast was achieved essentially as described (Klein et al., 1989a; Bartel et al., 1993a) with only minor modifications.

Plasmid Constructions

DNA fragments encoding the *E. coli* dnaB and dnaC genes were generated by PCR using genomic DNA isolated from *E. coli* strain W3110 (obtained from F. Neidhart, University of Michigan, Ann Arbor, Mich.; see Hill and Harnish, 1981). PCR primers were designed to contain restriction sites that permit in-frame fusions with the proteins encoded by the GAL4-based plasmids pAS2 and pACT. The PCR primers used to amplify the 1.4 kb dnaB open reading frame were RDK614 (CTCCATTCATATGGCAGGAAA), a sense primer designed to the amino terminus, including an Nde I site, and the antisense primer RDK615 . (GCATTTGGATCCTTGATAAGTG), designed to the carboxyl terminus, including a BamHI site. The restriction sites at the 3' ends of RDK614 and RDK615 were compatible with the multiple cloning site of the two-hybrid vector, pAS2, containing the GAL4-DNA binding domain. Internal sense (RDK 616; CCGGGTAAACACCGGTTATG) and antisense (RDK617; CATAACCGGTGTTTACCCCCGG) primers were used to confirm the specificity of the resulting fragment.

Amplification of the dnaC open reading frame was accomplished with primers RDK612

(ACCAGGATCCAGAGGGTAACGATG), a sense primer to the amino terminus that includes a BamHI site, and RDK613 (ACCGCTCGAGAAACGGGATT), an antisense primer to the carboxyl terminus that includes an XhoI site. Internal sense (RDK618; GATACCTTCAGGAATAGCGG) and antisense (RDK619; CCGCTATTCCTGAAGGTATC) primers were used to confirm the identify of the 700 bp PCR fragment encoding the dnaC open reading frame. Amplification of the DnaG open reading frame was accomplished with primers RDK 711 (GGGGCTTCCGAATTCGCCTCTTCG) an antisense primer to the carboxyl terminus that includes an EcoR1 site and RDK 717 (CAACAAATTAGGATCCTTGATGACAGCC) a sense primer to position 1430 of the gene sequence, GenBank accession number V00274, that encompasses the p16 segment of the gene which is reported to bind to DnaB. The PCR products encoding DnaB, DnaC and DnaG were cloned into pCRII. Verification of the correct orientation and sequence of the desired fragments was obtained by nucleotide sequence analysis of the 5' and 3' regions of inserts in the resulting plasmids, pCRII-dnaB, pCRII-dnaC, and pCR11-dnaG which revealed the presence of the introduced sites. The size of the inserts in these clones was verified by restriction enzyme digestions and PCR using primers RDK 616+RDK 617 for dnaB, and RDK618+RDK619 for dnaC and RDK718+711for dnaG.

The GAL4-DNA binding domain vector pAS2 was digested with NdeI and BamHI, the reaction mixture fractionated through a 0.8% agarose gel and the linear vector purified. The plasmid pCRII-dnaB was digested with Nde I and BamHI, the reaction mixture was fractionated through a 0.8% agarose gel and the 1.4 kbp fragment purified. The 1.4 kbp fragment was cloned into the linearized pAS2 vector. The resulting plasmid, pAS2-dnaB, was further characterized by restriction enzyme digestions, PCR and sequence analysis, confirming an in-frame fusion with the GAL4-DNA binding domain. The GAL4-activation domain vector pACTII was digested with BamHI and XhoI and the linearized vector purified as above. The plasmid pCRII-dnaC was digested with BamHI and XhoI and the 700 bp fragment purified and cloned into the linearized vector. The resulting plasmid, pACTII-dnaC, was characterized by restriction enzyme digestion, PCR and nucleotide sequence to confirm an in-frame fusion of dnaC with the GAL4-activation domain. The plasmid, pCRII-dnaG was cleaved with BamHI and EcoR1 and the released fragment purified away from the linearized vector. The plasmid, pACTII, was cleaved with BanHII and EcoR1 , purified as described above. The fragment isolated from pCRII-dnaG was ligated into the linearized pACTII vector. The resulting plasmid, pACTII-dnaG was characterized by restriction digests, PCR and nucleotide sequencing to confirm an in-frame fusion of dnaG with the GAL4 activation domain.

β-galactosidase Filter Assays

Filter assays to detect the expression of β-galactosidase by transformed yeast were conducted as described by (Bartel et al., 1993a).

Measures of Activity of the Invention

Yeast strains HF7c, SFY526, Y190 and Y166 (Table 1) were each co- transformed with all 4 combinations of pAS2 and PACTII containing the dnaB/dnaC inserts, including: pAS2+pACTII; pAS2+pACTII-dnaC; pAS2-dnaB+pACTII and pAS2-dnaB+pACTII-dnaC. In addition, each was co-transformed with the positive control plasmids pVA3+pTD1 (p53:SV40 large T antigen interaction). All transformations were plated on minimal medium lacking tryptophan and leucine. The resulting transformants were assayed for expression of β-galactosidase using the filter assay method. Transformants that received pAS2-dnaB+pACTII-dnaC uniformly showed significant color change in the filter assay within 3 hours in all 4 strains. The same result was obtained for the p53:SV40 large T antigen controls pVA3+pTD1. All other transformants were negative for β-galactosidase expression except, for those containing pAS2-dnaB, either as a single plasmid or paired with pACTII. The pAS2-dnaB transformants exhibited a slight positive color change after 24 hrs, indicating a low level of transcription activation.

The possibility that transcription activation occurred non-specifically at the minimal promoter in the reporter cassettes is negligible; the HF7c LacZ reporter gene was expressed, as well as the reporter gene in the other strains, even though HF7c contains the CYC1 minimal promoter, whereas the other strains contain variants of the GAL1 minimal promoter. However, this control did not eliminate the possibility that transcription activation was non-specifically attained by a dnaB:dnaC interaction near the amino terminus of the LacZ gene in all strains.

To test this possibility, we assayed transcription activation of the HIS3 and URA3 reporter genes by monitoring growth on selective medium. HF7c and Y190 transformants were tested for expression of HIS3 by plating cells on minimal medium lacking tryptophan, leucine and histidine. Untransformed Y190 cells showed slight growth, which could be blocked by adding 3-aminotriazole, an inhibitor of the HIS3 gene product (imidazoleglycerolphosphate dehydratase) to a final concentration of 10 mM (see Klopotowski and Wiater, 1965; Durfee et al., 1993). Untransformed HF7c cells showed no background growth on histidine-free medium. In both strains, transformants containing pAS2-dnaB+pACTII-dnaC showed growth equal to that of cells plated on minimal medium supplemented with histidine. No other transformants, including those containing pAS2-dnaB, grew in the selective medium. Y166 transformants were assayed for expression of the URA3 reporter gene by monitoring growth on minimal medium plates lacking tryptophan, leucine and uracil. Only Y166 transformed with pAS2-dnaB+pACTII-dnaC grew as well as plated on minimal medium supplemented with uracil. These data are summarized in Table 2. Plate assay results were reproduced in liquid culture in every case (data not shown).

The same experimental strategy was applied to demonstrate the interaction between DnaG and DnaB; in addition to DnaB and DnaB.

Multinle Target Screen (MTS).

Yeast strains dependent on the interaction of dnaB:dnaC; and dnaB:dnaG were added to the wells of a microtiter dish. Compounds were added and preincubated for a time. Minimal medium lacking tryptophane, leucine and uracil were added to the wells along with FOA and uracil.

Three compounds were identified that inhibited the interaction of DnaB::DnaC in the yeast two hybrid system as described above. These three compounds in addition to four others blocked the interaction of DnaB::DnaC using the yeast screening method as described above. In this case compounds that blocked the reporter gene URA3 were scored by the inability of the individual yeast strains to grow in medium lacking uracil.

To test whether inhibition of the DnaB::DnaC and/or DnaB::DnaG interaction would overcome the toxic effects of 5-FOA yeast strains (Y166) dependent on the interaction of B:C and/or B:G were preincubated with compound in YMM lacking FOA and uracil. Approximately 30 yeast cells were used per microtiter well. After 5 hours aliquots of FOA plus uracil were added to the cultures and incubated for 48 hours. Cell growth was scored visually, looking for a cell pellet in the bottom of the microtiter wells. No growth was seen in those wells containing yeast dependent in DnaB::DnaC and/or DnaB::DnaG without inhibitor. Growth was seen in wells containing yeast dependent on DnaB:DnaC and /or DnaB::DnaC that were preincubated with inhibitor.

These results show that inhibition of the protein:protein interaction responsible for the synthesis of the URA3 gene product alleviated the toxic effect of 5FOA by lowering the level of the URA3 reporter gene product in the cell.

Several strains of Y166 dependent on protein:protein interactions were mixed in microtiter wells, specifically, DnaB; DnaC; DnaB; DnaG and p53:SV40LT. The mixtures were preincubated with inhibitors as described above and scored for growth after 48 hours. Mixtures that had been preincubated with the specific inhibitory compounds showed significant growth in the presence of FOA and uracil. Those yeasts not preincubated were severely inhibited. These results show the system would work for more than one yeast strain dependent on a protein:protein interaction.

A summary of the experimental strategy for demonstrating the interaction of DnaB and DnaA; DnaB and DnaB; DnaB and DnaC; and DnaB and DnaG and are shown in FIG. 1. FIG. 2 provides a summary of the strategy for a Multiple Target Screening System. All figures and other illustrations in this document are intended to ease the readers ability to understand and appreciate the invention, they are not intended to limit the invention in any way.

TABLE 1

| Strain | Genotype | Reporter Cassette |
|---|---|---|
| Y190 | a gal4, gal80, *his* 3, trp 1-901, *ade* 2-101, *ura* 3-52, leu 2-3, -112, *lys* 2, URA3::GAL→lacZ, LYS::GAL→HIS3, cyh$^r$ | GAL→lacZ<br>GAL→HIS3 |
| Y166 | a gal4, gal80, *his* 3, *trp* 1-901, *ade* 2-101, *ura* 3-52, leu 2-3, -112, *lys* 2, URA3::GAL→lacZ, LYS::GAL→URA3, cyh$^r$ | GAL→lacZ<br>GAL→URA3 |
| SFY526 | a, *ura* 3-52, *his* 3-200, *ade* 2-101, *lys* 2-801, *trp* 1-901, leu 2-3, -112, can$^r$, gal4-542, gal80-538, URA3::GAL1→lacZ | GAL1→lacZ |
| HF7C | ura 3-52, *his* 3-200, *lys* 2-801, ade 2-101, *trp* 1-901, leu 2-3, -112, gal4-542, gal80-538, LYS2::GAL1→HIS3, URA3::GAL4$_{(UAS)3}$CYC1→lacZ | GAL1→HIS3 |

Strains Y190 and Y166 were obtained from Stephen J. Elledge, Baylor College of Medicine, Houston, Tex. See, Harper, et al. (1993) Cell 75: 805–816. Strain SFY526 was obtained from Stanley Fields, State University of New York, Stony Brook, N.Y. See, Bartel et al. (1993b) *BioTechniques* 14: 920–924. Strain HF7C was purchased from Clontech Laboratories, Palo Alto, Calif. See, Feilotter, H. E., et al. (1994) *Nucleic Acids Res.* 22: 1502–1503. Comparable, similar, related, functional yeast strains, obvious to one skilled in the art are also embodied by this invention.

TABLE 2

TRANSCRIPTION ACTIVATION

| Protein Pair | β-galactosidase[2] | Auxotrophic Reporter[1] |
|---|---|---|
| calcineurin A::B[3] | ++++ | + |
| p53::SV40LT[4] | +++ | + |
| SNF1::SNF4[5] | ++ | + |
| DnaB::DnaC[6] | +++ | + |
| DnaB | +/0 | 0 |
| DnaC | 0 | 0 |
| DnaB::GalACT[7] | +/0 | 0 |
| DnaC::Gal db[8] | 0 | 0 |
| Gal db::GalACT | 0 | 0 |
| DnaB::DnaG[9] | +++ | + |
| p53::DnaG | 0 | 0 |
| DnaB::DnaB[10] | +++ | + |

[1]Y166 is GAL1→URA3: Y190 and HF7c are GAL1→HIS3 (+ is growth, 0 is no growth)

[2]Y166, Y190 and SFY526 are GAL1→lacZ; HF7c is CYC1→lacZ with GAL4$_{UAS}$ ("+" indicates the time of color change, +/0 is more than 24 hours, ++ is 12 hours, +++ is 3 hours and ++++ is 1 hour.)

Fusion proteins were expressed from plasmids:

[3]calcincurin A::B were plasmids p-clacineurin A and p calcineurin B

[4]p53::SV40LT were pVA3 and pTD1

[5]SNF1::SNF4, were pAS1-SNF1(pSE 1112) and pACT-SNF4(pSE1111)

[6]DnaB::DnaC, were pAS2-dnaB and pACT11-dnaC

[7]GalACT, was pACT11

[8]Gal db (bd is DNA binding domain), was pAS2 (DnaG was tested using Y166)

[9]DnaG, was pACT-dnaG (DnaG was tested using Y166)

[10]Dna::DnaB, were pAS2-dnaB and pACT11-dnaB

SEQUENCE LISTING

```
(1) GENERAL INFORMATION:

   (iii) NUMBER OF SEQUENCES: 10


(2) INFORMATION FOR SEQ ID NO:1:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear
```

-continued (iii) HYPOTHETICAL: NO (iv) ANTI-SENSE: NO (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:1:

CTCCATTCAT ATGGCAGGAA A 21

(2) INFORMATION FOR SEQ ID NO:2:

(i) SEQUENCE CHARACTERISTICS:
(A) LENGTH: 22 base pairs
(B) TYPE: nucleic acid
(C) STRANDEDNESS: single
(D) TOPOLOGY: linear (iii) HYPOTHETICAL: NO (iv) ANTI-SENSE: YES (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:2:

GCATTTGGAT CCTTGATAAG TG 22

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: linear (iii) HYPOTHETICAL: NO (iv) ANTI-SENSE: YES (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:3:

CCGGGTAAAC ACCGGTTATG 20

(2) INFORMATION FOR SEQ ID NO:4:

(i) SEQUENCE CHARACTERISTICS:
(A) LENGTH: 22 base pairs
(B) TYPE: nucleic acid
(C) STRANDEDNESS: single
(D) TOPOLOGY: linear (iii) HYPOTHETICAL: NO (iv) ANTI-SENSE: YES (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:4:

CATAACCGGT GTTTACCCCC GG 22

(2) INFORMATION FOR SEQ ID NO:5:

-continued (i) SEQUENCE CHARACTERISTICS:
(A) LENGTH: 24 base pairs
(B) TYPE: nucleic acid
(C) STRANDEDNESS: single
(D) TOPOLOGY: linear (iii) HYPOTHETICAL: NO (iv) ANTI-SENSE: NO (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:5:

ACCAGGATCC AGAGGGTAAC GATC 24

(2) INFORMATION FOR SEQ ID NO:6:

(i) SEQUENCE CHARACTERISTICS:
(A) LENGTH: 19 base pairs
(B) TYPE: nucleic acid
(C) STRANDEDNESS: single
(D) TOPOLOGY: linear (iii) HYPOTHETICAL: NO (iv) ANTI-SENSE: YES (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:6:

ACCGCTCGAG AAACGGGAT 19

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (iii) HYPOTHETICAL: NO (iv) ANTI-SENSE: NO (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:7:

GATACCTTCA GGAATAGCGG 20

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (iii) HYPOTHETICAL: NO (iv) ANTI-SENSE: YES (vi) ORIGINAL SOURCE:
(A) ORGANISM: Escherichia coli
(B) STRAIN: Synthetic Oligonucleotide Primer (xi) SEQUENCE DESCRIPTION: SEQ ID NO:8:

-continued

```
CCGCTATTCC TGAAGGTATC                                                  20

(2) INFORMATION FOR SEQ ID NO:9:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

   (iii) HYPOTHETICAL: NO

    (iv) ANTI-SENSE: YES

    (vi) ORIGINAL SOURCE:
          (A) ORGANISM: Escherichia coli
          (B) STRAIN: Synthetic Oligonucleotide Primer

    (xi) SEQUENCE DESCRIPTION: SEQ ID NO:9:

GGGGCTTCCG AATTCGCCTC TTCG                                             24

(2) INFORMATION FOR SEQ ID NO:10:

     (i) SEQUENCE CHARACTERISTICS:
          (A) LENGTH: 28 base pairs
          (B) TYPE: nucleic acid
          (C) STRANDEDNESS: single
          (D) TOPOLOGY: linear

   (iii) HYPOTHETICAL: NO

    (iv) ANTI-SENSE: NO

    (vi) ORIGINAL SOURCE:
          (A) ORGANISM: Escherichia coli
          (B) STRAIN: Synthetic Oligonucleotide Primer

    (xi) SEQUENCE DESCRIPTION: SEQ ID NO:10:

CAACAAATTA GGATCCTTGA TGACAGCC                                         28
```

We claim:

1. A method for identifying useful compounds comprising:

a) the identification of about 1 to 20 protein::protein interactions of interest, where the protein::protein interactions are indicated X::Y, where protein(s) X and protein(s) Y interact with each other at the cellular level, where the protein(s) X and protein(s) Y may be the same or different proteins, b) the cloning of one set of proteins, either X or Y, as fusions, or as a set of fusions, to the DNA binding domain of the DNA that codes for a transcription activator protein, c) the cloning of the other set of proteins, either X or Y, as fusions, or as a set of fusions, to the DNA activation domain of the DNA that codes for a transcription activator protein, d) the maintaining of the sets of fusions as extrachromosomal elements in cells or the maintaining of the sets of fusions integrated in a yeast chromosome, where the extrachromosomal elements may be plasmids, e) the introduction of said sets of fusions into several yeast screening strains, said yeast screening strains comprising one or more reporter gene cassette(s), said reporter gene cassette(s) comprising a reporter gene, that is URA3 and comprising a DNA binding site specific to the DNA binding domain of the DNA coding region for said transcription activator protein, and said reporter gene expressed by said yeast screening strains produces a product that converts, 5' Fluoro-orotic acid (FOA), a substance that is non-toxic to the yeast screening strain into a substance that is toxic to the yeast screening strain, f) growing the yeast in the presence of test compounds, where the test compounds are the compounds to be assayed, and a) growing the yeast in selective medium, where the medium contains material needed for growth; or b) growing the strains, where the strains produce a measurable protein; or c) growing the strains, where the medium contains a non-toxic compound that can be converted by the product of the reporter gene into a substance that is toxic to the yeast screening strain, g) selecting compounds that inhibit the expression of the reporter gene, h) measuring said selected compounds that inhibit the expression of the reporter gene in a yeast testing strain, said yeast testing strain being isogenic with said yeast screening strain, and comprising a protein pair, protein A::protein B, where protein A and protein B, are proteins, the same or different from each other, and where protein(s) A and protein(s) B are the same or different from protein(s) X and protein(s) Y, and where protein pair, protein A::protein B are required by said yeast testing strain in order to activate said reporter gene and where said yeast testing strain is either dependent for growth upon the protein produced by said reporter gene, or where said yeast testing strain produces a protein by the reporter gene that is measurable, i) selecting compounds that inhibit the growth of the screening strain but do not either: inhibit the growth of the testing strain or inhibit the measurable reporter gene.

* * * * *